United States Patent [19]

Green et al.

[11] Patent Number: 5,682,726

[45] Date of Patent: Nov. 4, 1997

[54] METHOD FOR FORMING AND PACKAGING IONTOPHORETIC DRUG DELIVERY PATCHES AND THE LIKE TO INCREASE STABILITY AND SHELF-LIFE

[75] Inventors: Philip G. Green, Cliffside Park; Ronald J. Clark, Hewitt, both of N.J.; Bernt Fredrik Julius Broberg, Trosa, Sweden

[73] Assignee: Becton Dickinson and Company, Franklin Lakes

[21] Appl. No.: 730,948

[22] Filed: Oct. 16, 1996

Related U.S. Application Data

[63] Continuation of Ser. No. 316,741, Sep. 30, 1994, abandoned.

[51] Int. Cl.⁶ .......................... B65B 29/00; B65B 31/02; B65B 55/00
[52] U.S. Cl. .................... 53/433; 53/453; 53/474
[58] Field of Search .................... 53/433, 432, 511, 53/510, 454, 453, 559, 560, 474, 475, 473, 396; 604/20; 424/449, 448, 447

[56] References Cited

U.S. PATENT DOCUMENTS

| | | | |
|---|---|---|---|
| 2,775,080 | 12/1956 | Stim et al. | 53/454 X |
| 3,353,325 | 11/1967 | Jensen et al. | 53/433 |
| 3,481,100 | 12/1969 | Bergstrom | 53/433 |
| 3,814,095 | 6/1974 | Lubens | 128/260 |
| 4,722,726 | 2/1988 | Sanderson et al. | 604/20 |
| 4,820,263 | 4/1989 | Spevak et al. | 604/20 |
| 4,911,707 | 3/1990 | Heiber et al. | 424/449 |
| 4,917,676 | 4/1990 | Heiber et al. | 424/449 |
| 4,927,408 | 5/1990 | Haak et al. | 604/20 |
| 4,995,217 | 2/1991 | Francis, Jr. | 53/474 X |
| 5,084,008 | 1/1992 | Phipps | 604/20 |
| 5,110,599 | 5/1992 | Anhausser et al. | 424/449 |
| 5,264,224 | 11/1993 | Anhausser et al. | 424/467 |

FOREIGN PATENT DOCUMENTS

| | | |
|---|---|---|
| 303025 | 3/1989 | European Pat. Off. |
| 84 18 928 U | 11/1985 | Germany |
| WO-A-93/20787 | 10/1993 | WIPO |

OTHER PUBLICATIONS

Database WPI, Section Ch, Week 8849, Derwent Publications Ltd., London, GB; Class A12, AN 88–351245 & JP, A,63 264 520 (Nippon Oils & Fats KK), Nov. 1, 1988.

Patent Abstracts of Japan, vol. 13, No. 72 (C–570), Feb. 17, 1989 & JP,A,63 264520 (Nippon Oils & Fats Co. Ltd.), Nov. 1, 1988.

Database WPI, Section Ch, Week 9431, Derwent Publications Ltd., London, GB; Class A12, AN 94–252711 & JP,A,06 183 980 (Sekisui Chem. Ind. Co. Ltd.), Jul. 5, 1994.

Patent Abstracts of Japan, vol. 18, No. 528 (C–1258), Oct. 6, 1994 & JP,A,06 183980 (Sekisui Chem. Co. Ltd.), Jul. 5, 1994.

Chemical Abstracts, vol. 122, No. 12, Mar. 20, 1995, Columbus, Ohio, US; abstract No. 142527, Tamaki Y. et al., 'Manufacture of aspirin containing transdermal adhesive tapes in bags'.

Primary Examiner—James F. Coan
Attorney, Agent, or Firm—Allen W. Wark, Esq.

[57] ABSTRACT

A method for forming and packaging an iontophoretic patch in an inert atmosphere to provide increased shelf-life. The method includes a number of sub-assemblies for forming a well in a laminate material, forming the reservoir and dosing the reservoir, sealing the laminate material and another laminate material together to form a continuous web from which the individual patches are cut. In addition, the patch can be subsequently enclosed in an individual package. In this way, the patch and/or package provides a commercially suitable shelf-life to the drug-filled patch stored therein.

10 Claims, 3 Drawing Sheets

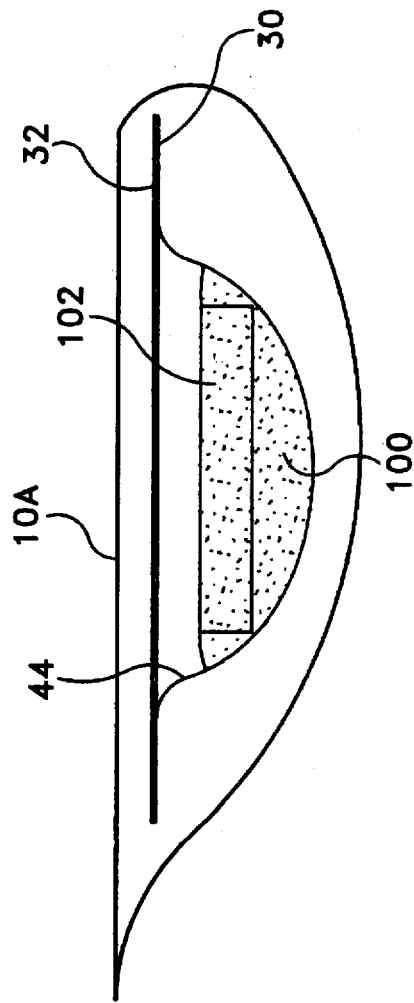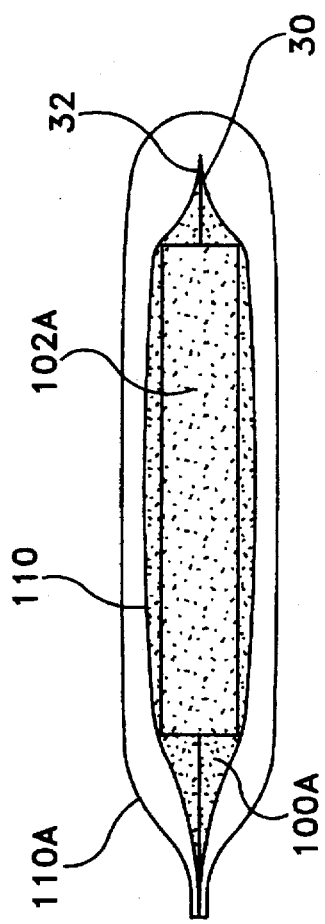

METHOD FOR FORMING AND PACKAGING IONTOPHORETIC DRUG DELIVERY PATCHES AND THE LIKE TO INCREASE STABILITY AND SHELF-LIFE

This application is a continuation of application Ser. No. 08/316,741, filed Sep. 30, 1994, and now abandoned.

FIELD OF THE INVENTION

The present invention generally relates to iontophoresis, and more specifically relates to a method of forming and packaging iontophoretic devices for delivering drugs or medicines to patients transmdermally, i.e., through the skin, to increase stability and shelf-life of the medicaments loaded therein.

BACKGROUND OF THE INVENTION

Transdermal drug delivery systems have, in recent years, become an increasingly important means of administering drugs. Such systems offer advantages clearly not achievable by other modes of administration such as avoiding introduction of the drug through the gastro-intestinal tract or punctures in the skin to name a few.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using iontophoresis, for example, which according to Stedman's Medical Dictionary, is defined as "the introduction into the tissues, by means of an electric current, of the ions of a chosen medicament."

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes—an anode and a cathode. Usually, electric current is driven from an external supply into the skin at the anode, and back out at the cathode. Accordingly, there has been considerable interest in iontophoresis to perform delivery of drugs for a variety of purposes. Two such examples, involve the use of Novocaine, which is usually injected prior to dental work to relieve pain, and Lidocaine, which is usually applied as a topical, local anesthetic.

However, several disadvantages and limitations have been associated with the use of such devices, including storage stability as a result of the drug not being in a form suitably stable to provide a commercially practical shelf life. Upon storage for extended periods, the therapeutic agents can degrade and become less potent as a result, for example, of oxidation of the medicament. Accordingly, such devices have been generally impractical for use on outpatients and in doctor's offices, since the products do not have sufficient shelf life.

Several of the prior passive type devices have attempted to overcome or minimize one such limitation, i.e., shelf life, by including a "burstable" member to isolate or separate the drug as disclosed in U.S. Pat. Nos. 4,911,707 (Heiber et al.) and 4,917,676 (Heiber et al.). However, limitations remain with respect to the use of such devices, particularly when "bursting" the member. During this event, the drug would be mixed with the activating solution which may result in reducing the dose efficiency of the device or incomplete mixing.

Another attempt to overcome this problem has included adding the drug to the device immediately prior to use as disclosed, for example, in U.S. Pat. No. 4,722,726 (Sanderson et al.), by injecting the drug into a chamber. However, other limitations remain with respect to the use of such devices, particularly when injecting the drug. During this event, the device is difficult to use, especially by persons who are handicapped or infirmed by some disability or limitation.

Thus, there has been a need for a method of forming and packaging iontophoretic devices, and in particular drug filled patches, which would eliminate the problems and limitations associated with the prior devices and methods discussed above, most significant of the problems being associated with storage of the device, i.e., shelf-life of the medicament loaded therein.

SUMMARY OF THE INVENTION

In contrast to the prior devices and methods discussed above, it has been found that a method for forming and packaging iontophoretic devices particularly suited for providing a commercially suitable shelf-life to the drug-filled patch contained therein can be constructed in accordance with the present invention.

The method of forming and packaging an iontophoretic patch of the present invention including a drug filled reservoir includes the steps of forming a well in a first laminate material, placing a reservoir material in the well and placing at least a portion of a dose of medication therein to fill the reservoir material, placing a second laminate material over the well, sealing the laminate materials together to form a continuous web, so that a chamber is formed therebetween having an inert gas contained in the chamber, and cutting an individual patch from the web.

In the preferred embodiment, the step of sealing the laminate materials together incudes the step of forming a heat seal around a periphery of the well. Also, the step of cutting the patch from the continuous web includes die cutting. In addition, the method further includes the steps of forming a drug reservoir from the reservoir material and placing any remaining portion of the medicament in the well. Further, the steps of placing the medicament in the well take place in an inert atmosphere.

In the alternative, the method of forming and packaging an iontophoretic patch including a drug filled reservoir of the present invention may include the steps of placing a reservoir material on a first laminate material and dosing the reservoir material with at least a portion of a medicament to at least partially fill the reservoir material, sandwiching the reservoir material between the first laminate material and a second laminate material with the reservoir material positioned therebetween, sealing the laminate materials together to form a continuous web, so that a chamber is formed therebetween having an inert gas contained in the chamber, and cutting an individual patch from the web.

In addition, the step of dosing the reservoir takes place in an inert atmosphere. Also, the method further includes the step of enclosing the patch in a package.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 2 is an enlarged, cross-sectional, side view of the packaging of the present invention;

FIG. 2A is an enlarged, cross-sectional, side view of an alternative embodiment of the packaging of the present invention.

DETAILED DESCRIPTION OF THE PREFERRED EMBODIMENT

Figure 1:
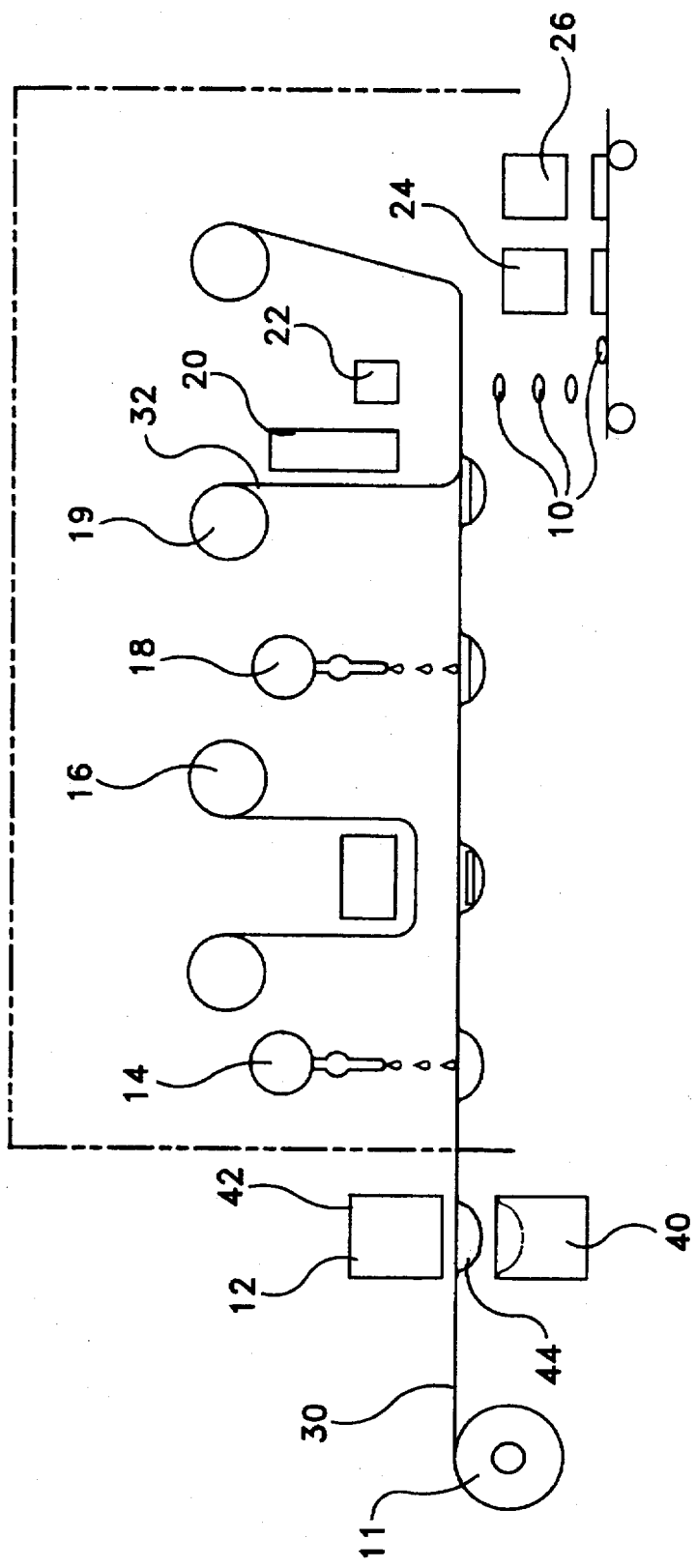
FIG. 1 is a schematic representation of a pilot-line illustrating the various steps for forming and packaging a iontophoretic patch in accordance with the method of the present invention.
Figure 3:
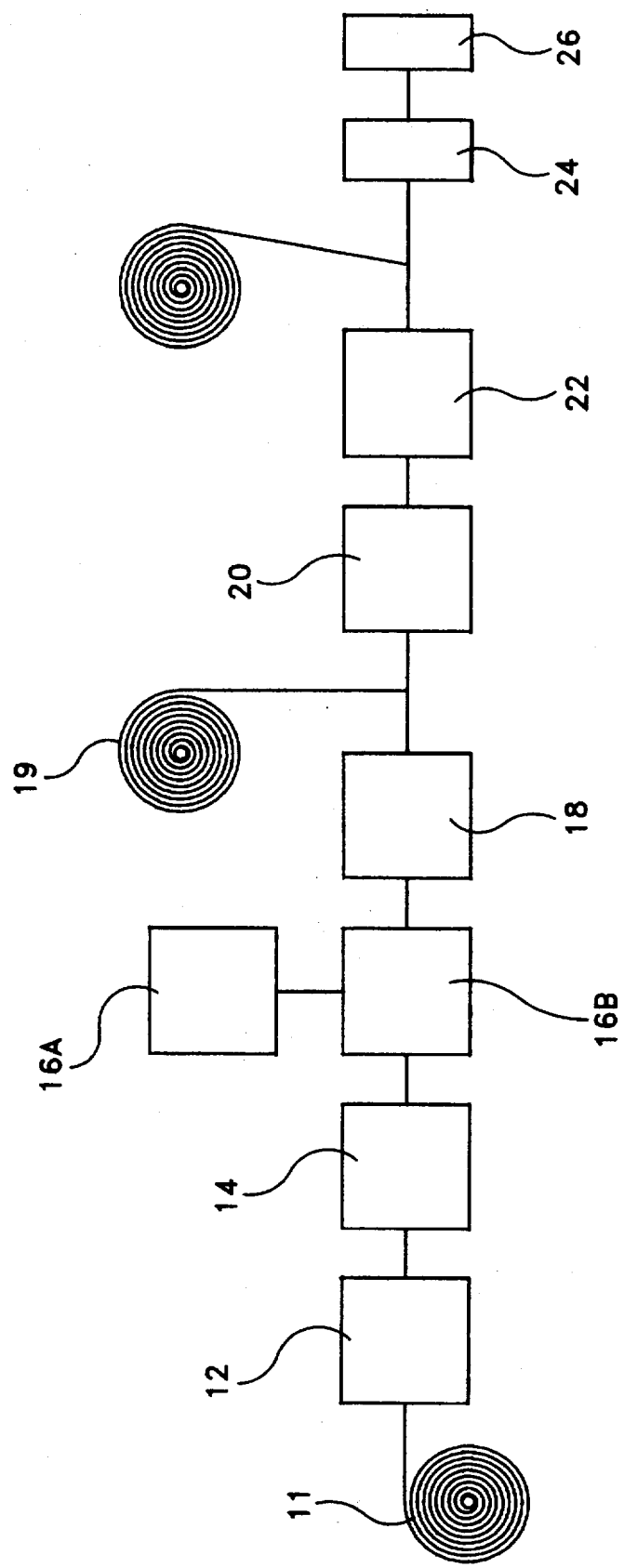
FIG. 3 is a logic flow diagram depicting the various steps of the method of the present invention.

The method of the present invention for forming and packaging iontophoretic devices, particularly drug filled patches, is illustrated in FIGS. 1–3.

Referring to FIG. 1, the method of the present invention generally includes applying the medicament to a reservoir within an inert atmosphere including, for example, inert gases such as nitrogen, carbon dioxide, and/or mixtures thereof such as 5–10% hydrogen/nitrogen. Specifically, a number of sub-assemblies 11, 12, 14, 16, 18, 19, 20, 22, 24 and 26 carry-out the various steps for forming the individual patches and packages 10A from laminate materials. Specifically, the system includes a sub-assembly 11 for continuously feeding a first laminate material 30, a sub-assembly 12 for forming a well in the backing material in which sub-assembly 14 preferably places a partial dose of the substance to be delivered such as a medicament 100, a sub-assembly 16 for forming a drug reservoir 102 and placing the reservoir in the well, a sub-assembly 18 for placing the remainder of the dose of the substance to be delivered, a sub-assembly 19 for feeding a second laminate material 32 including an electrode layer, a sub-assembly 20 for heat sealing the first and second laminate materials together with the drug filled-reservoir therebetween into a continuous web 34 with a chamber 104 formed thereby, and a final sub-assembly 22 for cutting the individual packages 10 from the continuous web. In addition, as illustrated in FIGS. 1 and 3, a sub-assembly 24 may be included for picking and placing the individual packages and a sub-assembly for enclosing or otherwise surrounding the patch 10 with an additional package 10A.

In the preferred embodiment of the packaging 10 illustrated in FIG. 2, the laminate material 30 is preferably 2–3 mil thick continuous roll of Scotch Pack™ film available from Minnesota Mining and Manufacturing Company ("3M"), St. Paul, Minn. Also, a heat seal coating may be provided on the laminate 30. In addition, it should be appreciated that a separate release liner (not shown) may be included along with a release coating thereon, or preferably, the release coating may be placed on one of the laminate materials. Preferably, the second laminate material 32 includes an electrode layer as disclosed, for example, in U.S. patent application Ser. No. 08/012,168, filed Feb. 2, 1993, the disclosure of which is hereby incorporated by reference in its entirety.

In an alternative embodiment illustrated in FIG. 2A, the step of forming a well is eliminated so that the reservoir 102A is sealed within an envelope formed between the laminate materials 30, 32.

As illustrated in FIG. 1, the sub-assembly 12 for forming the well includes a bottom plate 40 and a top plate 42, with at least one of the plates being movable in the vertical direction relative to the other plate as disclosed, for example, in U.S. patent application Ser. No. 08/067,638, filed May 26, 1993, the disclosure of which is hereby incorporated by reference in its entirety. The laminate material 30 passes between the plates 40, 42, which can be brought together by an actuating cylinder and a positive pressure provided against the laminate material to force the laminate material into a cavity beyond the point of elasticity of the laminate material to permanently form a well or dimple 44 in the laminate material, with the amount of pressure being applied depending upon the elastic strength of the laminate material, which in the case of the preferred material is 40 to 80 PSI. A vacuum may be drawn on the opposite side of the laminate material to facilitate forming of the blister.

As illustrated in FIG. 1, preferably a portion of the dose of medication 100 is applied to the laminate material 30 in the well 44 by sub-assembly 14 and the remainder applied by sub-assembly 18 as is well known in the art, which in the preferred embodiment may include positive displacement pumps. The dose of medication can be varied depending upon the substance used, which may, for example, include Epinephrine, Vitamin B12, dobutamine, Dopamine and the like. However, it should be appreciated that other substances suitable for being applied to the area may be utilized which are well known to those skilled in the art.

Thereafter, the laminate materials are brought together and heat sealed around the outer periphery of the well by sub-assembly 20 to form the continuous web 34, with the drug filled reservoir being sealed within a corresponding well. Next the continuous web is die cut by sub-assembly 22 to fabricate the individual packages 10 therefrom.

The materials and components used for constructing the various sub-assemblies are not essential to the present invention and may be made from a variety of commercially available components well known to those skilled in the art. Normally, manufacturers utilizing the method of the present invention will select the various materials and components, based upon price, availability and application.

Operation and Use

The operation of the system illustrated in FIG. 1 for practicing the method of the present invention will now be explained with reference to the flow diagram shown in FIG. 3 illustrating the various stations making up the sub-assemblies 11, 12, 14, 16, 18, 20, 22, 24 and 26.

As explained, the first laminate material 30 and the second laminate material 32 are continuously processed along a single track, with the first laminate being feed by sub-assembly 11 and passing through the sub-assembly 12 for forming the well 44 and the sub-assemblies 14 and 18, for dosing the medicament 100, and sub-assembly 16 for forming the reservoir 102 and sub-assembly 16B for placing the reservoir in the well 44, with the dose of medication being applied to fill or otherwise load the reservoir 102. Thereafter, the second laminate material 32 is feed along the track and the two are brought together and heat sealed by the sub-assembly 20 to form the continuous web 34 from which the individual packages 10 are die cut.

Thereafter, the patch 10 can be picked and placed by sub-assembly 24 and again placed in an additional package 10A by sub-assembly 26.

It should be appreciated, that it is essential to the present invention that the steps of dosing the reservoir be carried out in an inert environment by assemblies 14 and 18, and preferably, including the steps of forming and placing the reservoir 102 and sealing the laminate materials by sub-assemblies 16A, 16B and 20.

In addition, the patch 10 and/or the package 10A may also contain an oxygen scavenger such as sodium metalsulphite to remove oxygen. An other example, may include the use of palladium beads, which can be added to the patch and/or package containing a hydrogen and nitrogen mixture. In this way, oxygen entering will be converted to water on the surface of the bead. Also, it should be appreciated that instead of providing an inert atmosphere room or the like, the track can be engulfed in a laminar flow of the inert gas or the inert gas can be injected directly into the well 44 and/or the package 10A.

In addition, the packages 10 of the present invention can be fabricated or otherwise cut from the continuous web in a number of shapes other than that shown in the drawings. Also, the packages can be made in different sizes depending upon the medicament used, the duration of delivery and/or whether it is to be used by adults or infants.

While the preferred embodiments of the present invention has been described so as to enable one skilled in the art to practice the method of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A method of forming and packaging an iontophoretic patch including a drug filled reservoir comprising the steps of:

forming a well in a first laminate material;

placing a reservoir material in said well and placing at least a portion of a dose of medication therein to fill said reservoir material;

placing a second laminate material over said well;

sealing said laminate materials together to form a continuous web, so that a chamber is formed therebetween having an inert gas contained in said chamber; and cutting an individual patch from said web.

2. The method of forming and packaging an iontophoretic patch defined in claim 1, wherein said step of sealing said laminate materials together incudes the step of forming a heat seal around a periphery of said well.

3. The method of forming and packaging an iontophoretic patch defined in claim 1, wherein said step of cutting said patch from said continuous web includes die cutting.

4. The method of forming and packaging an iontophoretic patch defined in claim 1, further comprising the step of forming a drug reservoir from said reservoir material.

5. The method of forming and packaging an iontophoretic patch defined in claim 1, wherein said reservoir material includes a hydrophilic gel.

6. The method of forming and packaging an iontophoretic patch defined in claim 1, further comprising the step of placing any remaining portion of said medicament in said well.

7. The method of forming and packaging an iontophoretic patch defined in claim 6, wherein said steps of placing said medicament in said well take place in an inert atmosphere.

8. A method of forming and packaging an iontophoretic patch including a drug filled reservoir comprising the steps of:

placing a reservoir material on a first laminate material and dosing said reservoir material with at least a portion of a medicament to at least partially fill said reservoir material;

sandwiching said reservoir material between said first laminate material and a second laminate material with said reservoir material positioned therebetween;

sealing said laminate materials together to form a continuous web, so that a chamber is formed therebetween having an inert gas contained in said chamber; and cutting an individual patch from said web.

9. The method of forming and packaging an iontophoretic patch defined in claim 8, wherein said step of dosing said reservoir takes place in an inert atmosphere.

10. The method of forming and packaging an iontophoretic patch defined in claim 9, further comprising the step of enclosing said patch in a package.

* * * * *